United States Patent
Dresel et al.

(10) Patent No.: US 8,525,852 B2
(45) Date of Patent: Sep. 3, 2013

(54) METHOD AND DEVICE SELECTIVE PRESENTATION OF TWO IMAGES INDIVIDUALLY OR COMBINED AS A FUSION IMAGE

(75) Inventors: Holger Dresel, Altendorf (DE); Thomas Gossler, Erlangen (DE); Andreas Grimme, Erlangen (DE); Marion Hellinger, Uttenreuth (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 274 days.

(21) Appl. No.: 12/687,967

(22) Filed: Jan. 15, 2010

(65) Prior Publication Data
US 2010/0201708 A1 Aug. 12, 2010

(30) Foreign Application Priority Data
Jan. 16, 2009 (DE) .................. 10 2009 004 898

(51) Int. Cl.
G09G 5/00 (2006.01)
G06F 3/041 (2006.01)

(52) U.S. Cl.
USPC ........... 345/629; 345/156; 345/173; 715/244; 715/863

(58) Field of Classification Search
USPC ............... 345/629, 156, 173; 715/244, 779, 715/863
See application file for complete search history.

(56) References Cited

U.S. PATENT DOCUMENTS
6,323,846 B1  11/2001  Westerman et al.
2009/0021475 A1*  1/2009  Steinle et al. .................. 345/156
2010/0020133 A1*  1/2010  Ohashi et al. .................... 347/70
2010/0050133 A1*  2/2010  Nishihara et al. .............. 715/863
2010/0173678 A1*  7/2010  Kim et al. ....................... 345/173
2011/0078616 A1*  3/2011  Chaudhri et al. .............. 715/779
2011/0102458 A1*  5/2011  Takiguchi et al. ............. 345/629
2011/0185277 A1*  7/2011  Altman et al. ................. 715/244
2011/0273473 A1*  11/2011  Kim ............................... 345/629

OTHER PUBLICATIONS

"Surgical PACS Access", Brainlab.com, 2011.*
Brain_LAB, "Digital Lightbox—Multi-touch Display", dailymotion.com, Jun. 5, 2009.*
Printout of Website for BrainLab AG (2008).

* cited by examiner

Primary Examiner — Chante Harrison
(74) Attorney, Agent, or Firm — Schiff Hardin LLP

(57) ABSTRACT

In a method and device to show two different images (determined from a first image data set and a second image data set) of at least one imaging modality (in particular a medical imaging modality), the images can be presented together on a display device with a presentation area as a fusion image or as individual images. A detection arrangement associated with the display device detects a movement of at least one finger of a user on the or in the immediate proximity of the presentation area or a contact of the presentation area and, depending on the detection, produces a change of the presentation of the fusion image, or changes between an individual image presentation and fusion image presentation or between two individual image presentations. A change from the first image to the second image is produced based on a movement of at least one finger ensuing essentially parallel to the presentation area, or the display of the first image is produced or removed based on a movement of at least one finger ensuing essentially parallel to the presentation area, with the display of the second image not being altered by the movement.

16 Claims, 3 Drawing Sheets

METHOD AND DEVICE SELECTIVE PRESENTATION OF TWO IMAGES INDIVIDUALLY OR COMBINED AS A FUSION IMAGE

BACKGROUND OF THE INVENTION

1. Field of the Invention

The present invention concerns a method to show two different images (respectively determined from first and second image data sets) of at least one imaging modality (in particular a medical imaging modality), of the type wherein the images can be presented together on a display device with a presentation area as a fusion image or as individual images; and wherein a detection means associated with the display device detects a movement of at least one finger of a user on or in the immediate proximity of the presentation area or contact with the presentation area, and, depending on the detection, produces a change of the presentation of the fusion image, or changes between an individual presentation and fusion presentation or changes between two individual image presentations.

2. Description of the Prior Art

Fusion images are produced by a combination of two image data sets. The image data sets can originate from different and spatially separate imaging modalities (such as magnetic resonance tomography and positron emission tomography), or can originate from a combined device. It is also known, for magnetic resonance exposures, to overlay images that were acquired with different resonance frequencies atop one another as a fusion image. Overlaying images from measurements at the proton resonant frequency and the phosphorus or sodium resonant frequency is an example. The image data sets can have been acquired simultaneously or with a time offset. After a registration of the image data sets, a combined presentation as a fusion image is possible.

The combination of the different data sets is meaningful because every imaging modality has its own advantages and disadvantages, or the exposures at different resonance frequencies provide different information in the case of magnetic resonance tomography. While x-ray and computed tomography images allow a good depiction of bones, magnetic resonance tomography is superbly suited to show soft tissues. By contrast, metabolic processes can be shown particularly well by means of positron emission tomography.

In the presentation of fusion images there is a problem that an information loss occurs given an overlay of the image data, since image data from the respective component images naturally cannot be shown simultaneously at the same fusion image point. It is therefore known for a user to change the presentation type of the image by pressing a key or clicking on a control button with the mouse. Either one image data set can be masked out by this interaction, or the contrast of one or both image data sets can be varied. The necessity of making this intervention diverts the attention of user from the fusion image and a portion of the information that should be obtained by changing the presentation type is lost.

SUMMARY OF THE INVENTION

An object of the present invention is to provide a method of the aforementioned type in which an interaction of the user to change the presentation of a fusion image or its individual images without a loss of information is possible.

This object is achieved in such a method by implementing a change from the first image to the second image based on a movement of at least one finger of the user ensuing essentially parallel to a side of the presentation surface, or the display of the first image is implemented or removed based on a movement of at least one finger of the user that ensues essentially parallel to a side of the presentation area, with the display of the second image not being altered by the movement.

The user thus no longer interacts with an input unit separate from the display device showing the fusion image; rather, the changes are produced directly via the display device i.e., its presentation area. The user thus can keep his or her gaze on the presentation area of the display device while making a change of the presentation of the fusion image or its individual images. The user is no longer diverted from the fusion image, and the user can direct his or her full concentration on the fusion image even while changing the presentation of the fusion image. As an alternative to changing the presentation of the fusion image, the user can change between a presentation of the individual images of the fusion image as an individual image and as a fusion image. A single image of the fusion image is thus displayed or not dependent on a detected movement. As an additional alternative, a change between the individual images and the fusion image can be made by means of a detected movement. In this case, presentation of the fusion image is at least intermittently not provided. In these alternative embodiments as well, the user does not need to turn his or her gaze away from the presentation area, so the user can better concentrate on the shown image or images. Furthermore, the user can generate the fusion image by overlaying two individual images.

In one embodiment, a change from the first image to the second image is produced based on a movement at least one finger ensuing essentially parallel to the presentation area. The user wipes the first image to the side, so to speak, while the second image is newly presented on the display device. The finger or fingers can contact the presentation surface in the movement, but the movement can also be executed in proximity to the presentation area. The movement likewise occurs in the field of view of the user's eyes, which is why the user is not diverted.

Alternatively, the display of the first image is produced or removed based on a movement of at least one finger ensuing essentially parallel to the presentation area, with the display of the second image not being changed by the movement. It is thus possible to display the image in a static manner with morphological information while the image with dynamic information is activated and deactivated. For example, a magnetic resonance image can be displayed in a static manner as the second image. Morphological or anatomical information are contained in this second image. This information can be presented two-dimensionally and even three-dimensionally depending on the existing data set. In the case of a two-dimensional presentation, an image that was acquired by means of positron emission tomography is superimposed on the magnetic resonance image data set, for example. This image, also abbreviated as a PET image, provides information about metabolic processes. By superimposing the PET image over the magnetic resonance image, information in the magnetic resonance image is covered at the overlay points. In order to make the details of the magnetic resonance image visible again, the user must merely swipe the PET image to the side, so to speak, with a hand movement. Alternatively, depending on the length of the movement, the opacity of the PET image can be varied. This means that the transparency of the PET image can be varied linearly or in stages. The PET image thus appears to be transparent so that the magnetic resonance image under the PET image is visible. The opacity can be varied from a complete non-transparency to complete transparency. In this case it is necessary to detect both the direction and the length of the movement. Due to the directional dependency of the movement, the original opacity can be reestablished by a movement in the opposite direction.

The change that has occurred can advantageously be automatically canceled again after a specific time span. Usually, the user wants to continually view the presentation that he or she has selected. Only as an exception should the type of observation be changed, for example in order to make details in the second image visible or in order to show short-term metabolic processes in the form of the first image. In order to further unburden the user, an automatic resetting to the initial presentation is therefore available. The diversion of the user away from the actual fusion image thus can be additionally decreased.

The first image can have at least one featured (distinguished) region that can be selected in a positionally detected manner using the finger, to cause the presentation of the first image to be varied depending on a detected movement. This is, so to speak, a manner of image processing at the display device. This is possible when the image data sets have been non-rigidly registered with one another. For example, it is thereby possible to improve apparent presentation errors directly on the screen or on the presentation area. For this purpose, the first image has regions that can be moved as well by positioning of the finger on or above this region with subsequent movement. The shape of the image is hereby varied in order to compensate for possible registration errors. In particular, a region in the center of the first image can be provided that enables a movement of the entire first image and not only the movement of a sub-region of the image.

With particular advantage, at least one region can be provided at the edge of the presentation surface, starting from which a movement of at least one finger begins, and the presentation of the fusion image is varied in an area defined by the position of the finger depending on the selected region. Outside of the fusion image, one or more buttons can be positioned that can be selected (activated) with additional finger movement to cause a region in the first and/or second image presentation to be varied. For example, a button can be provided that, when selected, causes a region in the first image above a specific threshold relative to the signal intensity to be converted into a black-and-white image data set. Naturally, color combinations other than black-and-white are also possible. For example, a PET image that predetermines a measure for the metabolism can be divided into an active region and passive region with regard to the metabolism. However, the change of the presentation ensues only in the region that was detected by the movement of the finger in the horizontal or vertical direction. Alternatively, it is also possible to vary the entire first image by contacting the buttons, thus the region at the edge of the presentation area that changes the presentation of the fusion image. The variation can be canceled by again touching this same button.

The invention also concerns a device for image presentation, having a display device with a presentation area, a detection device, and a control device that is fashioned to implement the described method. The detection device can advantageously be formed by at least one infrared sensor.

DESCRIPTION OF THE PREFERRED EMBODIMENTS

Figure 1:
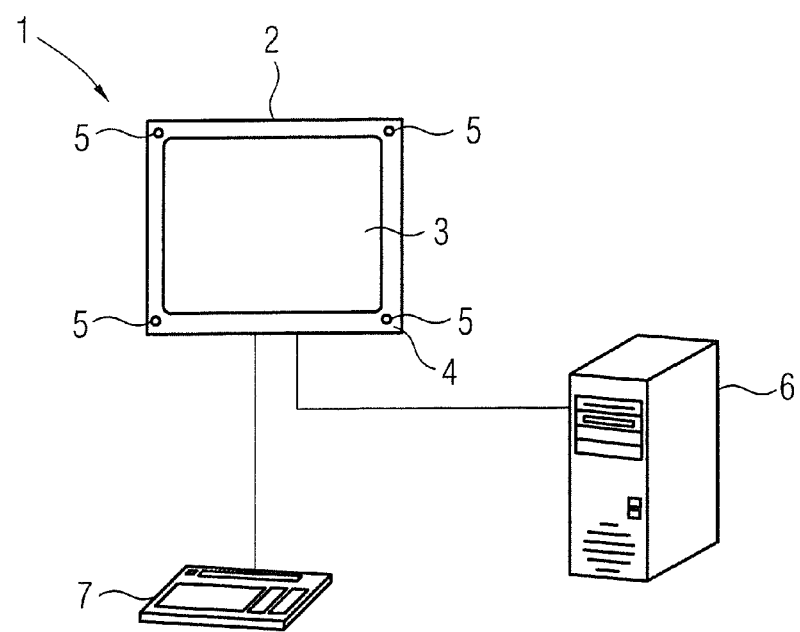
FIG. 1 schematically illustrates a device according to the invention for image presentation.

FIG. 1 shows a device for image presentation 1 that has a display device 2, a control device 6 and a keyboard 7. In addition to a presentation area 3, the display device also has a detection device 4 composed of multiple infrared sensors. The infrared sensors are fashioned to detect movements of a finger or multiple fingers. The detection device 4 can differentiate between the movement directions, pressing of a region of the presentation area, and the length of the movement of a detected finger or multiple detected fingers.

Figure 2:
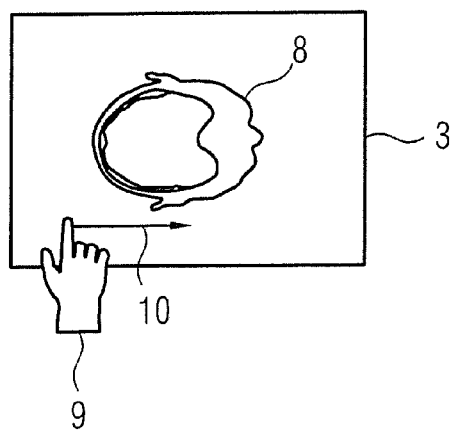
FIGS. 2 and 3 schematically illustrate the variation of the presentation in a first embodiment.
Figure 3:
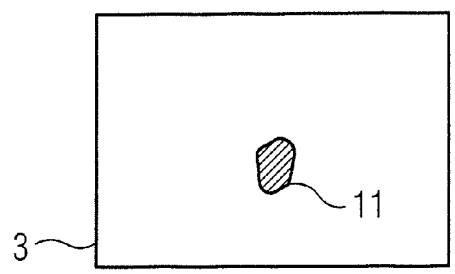

FIG. 2 shows a magnetic resonance (MR) image 8 that is shown on the presentation area 3. To change to the second image of the fusion image, the user must merely execute a movement with his to her hand 9 parallel to the presentation area, for example in the direction of the arrow 10. The amount of the movement should exceed a certain threshold; otherwise the length is not significant. After implementation of the movement, as shown in FIG. 3, the PET image 11 alone is shown. This is the second image of the fusion image. It is located at the point of the presentation area 3 at which it must be shown due to the registration with the MR image 8. The direction of the arrow 10, and therefore the movement to be detected, can alternatively also ensue vertically or in the opposite direction.

Figure 4:
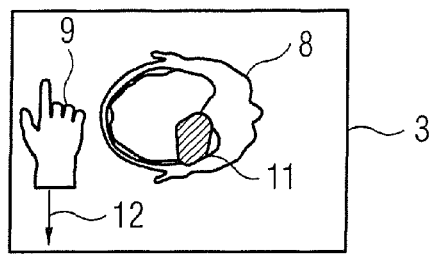
FIGS. 4 and 5 schematically illustrate the variation of the presentation in a second embodiment.
Figure 5:
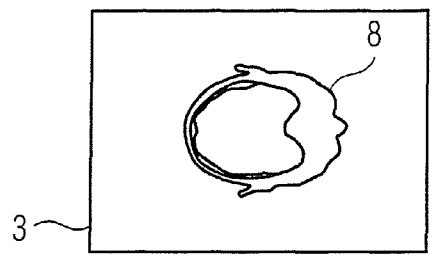
Figure 6:
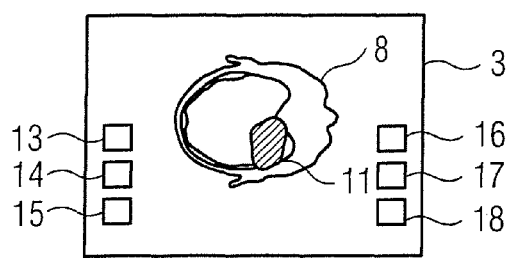
FIGS. 6 and 7 schematically illustrate the variation of the presentation in a third embodiment.

As an alternative to changing between the images of the fusion image, it is also possible to show the two images superimposed; see FIG. 4. By moving the hand 9 in the direction of the arrow 12, the PET image 11 is wiped out of the presentation area 3, so to speak. Accordingly, only the MR image 8 is still visible in FIG. 5. Since the overlaid presentation according to FIG. 4 is, however, the actual desired presentation form, and the PET image 11 should only be temporarily removed in order to be able to observe details of the MR image 8, the PET image 11 is displayed again automatically after a freely selectable time span. The user thus does not personally have to cause the display of the PET image 11 that is to be produced anyway.

As an alternative to the described possibilities of the presentation change, it is also possible to use the direction information of the movement of the hand 9 or its fingers. Assuming the presentation of a fusion image as in FIG. 4, a movement that essentially follows the direction of the arrow 12 is detected and the PET image 11 is accordingly no longer shown. A detected movement in the direction of the arrow 10 then produces a change of the presentation between the MR image 8 and the PET image 11, as is shown in FIGS. 2 and 3. If a (second) movement opposite to or in the direction of the arrow 12 is detected by the infrared sensors 5, the fusion image is shown visible again as in FIG. 4.

The fusion image, composed of an MR image 8 and a PET image 11, also can be varied in terms of the presentation of the individual images in addition to the possibilities already described above with regard to changing the display. For this purpose, buttons 13, 14, 15, 16, 17 and 18 are arranged on the edge of the presentation area 3. The buttons 13-18 represent regions of the presentation area 3; if a finger of a user touches or sweeps over or approaches the area of such a button, a movement of the hand 9 of the user should be provided with an additional functionality. The buttons 13-15 thereby relate to the MR image 8 and the buttons 16-18 relate to the PET image 11.

The buttons 13 and 16 produce a presentation of the corresponding image in only two colors, for example black and white. This differentiation is made using a threshold of the signal intensity. With regard to the PET image, the presentation then ensues divided into regions of higher and lower metabolic activity, and with regard to the MR image 8 the image is divided into regions of higher and lower signal intensity, and therefore essentially into regions of higher and lower spin density.

The buttons 14 and 17 produce a presentation of the respective image, analogous to the buttons 13 and 16, wherein the values below the threshold are however transparent and are thus depicted as invisible.

Figure 7:
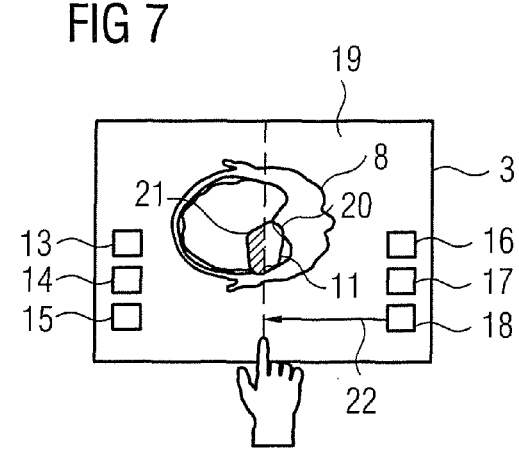

Finally, the buttons 15 and 18 produce a complete transparency of the region of the respective image that they refer to and that is limited by a movement of the hand 9. FIG. 7 shows how the selection of the button 18 with subsequent movement of the fingers of the hand 9 in the direction of the arrow 22 varies the presentation of the PET image 11. By the movement of the hand 9 and of the finger that is thereby detected, the presentation area 3 is divided up into a region 19 detected by the movement of the finger and a region that is not detected by this. The presentation of the PET image is varied within the region 19 detected by the movement of the finger. The region 20 is shown transparent according to the functionality linked with the button 18 while the region 21 remains in the original presentation. By moving the hand 9 further, the entire PET image could be shown transparent. The PET image data set 11 could also be divided in particular in a vertical direction into a transparent region 20 and a non-transparent region 21 by means of a forward movement of the hand 9 starting from the button 18. The division of the PET image data set can be reestablished by moving the hand back in the direction of the button 18, or also by leaving the presentation area 3.

Figure 8:
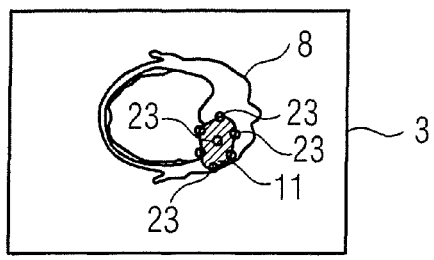
FIGS. 8 and 9 schematically illustrate the variation of the presentation in a fourth embodiment.
Figure 9:
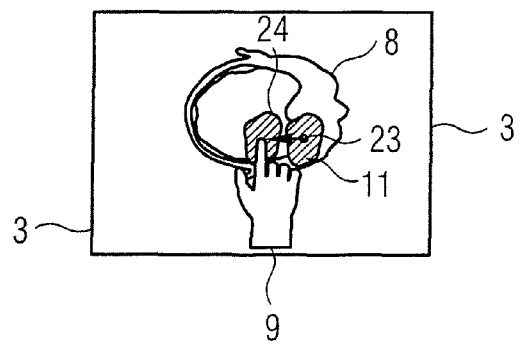

FIG. 8 shows a fusion image where an error has occurred in the registration of its individual images. In order to be able to correct this, the PET image 11 possesses regions 23 that can be selected via finger whose position is detected, wherein the presentation of the PET image is varied depending on a detected movement. If the distinguished region 23 located in the center of the PET image 11 is selected by a finger, for example, and the hand 9 moves onto this, the entire PET image thus follows the movement in the direction of the arrow 25 in order to then be shown as a registration-corrected PET image 24. The selection of the region 23 located in the center of the PET image 11 thus produces a displacement of the PET image; see FIG. 9.

Figure 10:
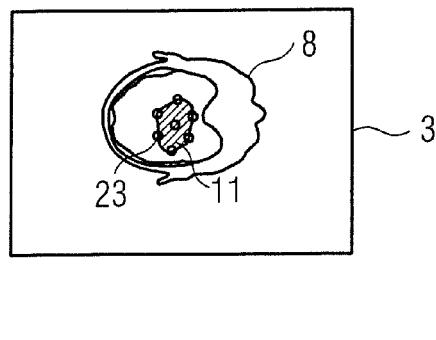
FIGS. 10 and 11 schematically illustrate the variation of the presentation in a fifth embodiment.
Figure 11:
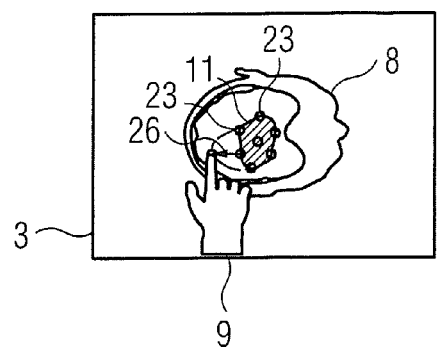

FIG. 10 shows a different situation: the PET image 11 itself is located at the correct point but a deformation of the PET image 11 has occurred via the registration. Therefore distinguished regions 23 are likewise located at the edge of the PET image 11, wherein the shape of the PET image 11 can be varied by its selection. This is shown in FIG. 11. A finger of the hand 9 selects a region 23 at the edge of the PET image 11 and the user moves the finger in the direction of the arrow 26. The distinguished region 23 is moved as well due to the movement of the finger and the shape of the PET image is accordingly modified.

A changing of the presentation of the fusion image based on an interaction of the user with the presentation area 3 is thus possible without diverting the user from the fusion image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for selectively presenting two different first and second images, respectively obtained from a first image data set and a second image data set that is different from said first image data set, either individually or combined as a fusion image, comprising the steps of:

in a computerized display device having a presentation area, said presentation area having a first side and a second side perpendicular to said first side, automatically detecting movement of at least one finger of a user over or in contact with a surface of said presentation area;

when one of said first or second images is currently displayed in said presentation area, as a currently-displayed image, and movement of said at least one finger in a direction parallel to said first side of said presentation area is detected by said computerized display device, in response to no more than said movement of said at least one finger in said direction parallel to said first side of said presentation area, automatically removing said currently displayed image from said presentation area and displaying only the other of said first and second images;

when one of said first and second images is currently displayed in said presentation area, as an initially displayed image, and movement of said at least one finger in a first direction parallel to said second side of said presentation area is detected by said computerized display device, in response to no more than said movement of said at least one finger in said first direction parallel to said second side of said presentation area, automatically adding the other of said first and second images to said initially displayed image in said presentation area to form a fusion image of said first and second images in said presentation area; and when said fusion image is displayed in said presentation area, and movement of said at least one finger in a second direction, opposite to said first direction, parallel to said second side of said presentation area is detected by said computerized display device, in response to no more than said movement of said at least one finger in said second directional parallel to said second side of said presentation area, removing the other of said first and second images from said fusion image to leave only said initially displayed image in said presentation area.

2. A method as claimed in claim 1 comprising, in said computerized display device automatically timing an elapsed time after changing from said currently displayed image to display of said other of said first and second images in said presentation area, and automatically reverting to presentation of said currently displayed image after a predetermined elapsed time.

3. A method as claimed in claim 1 comprising, in said computerized display device automatically timing an elapsed time after removal of said other of said first and second images from said fusion image, and automatically restoring presentation of said fusion image to said presentation area after a predetermined elapsed time.

4. A method as claimed in claim 1 comprising displaying said first image in said presentation area with a distinguished region that is selectable by detecting a position of said at least one finger relative to said surface of said presentation area, and modifying presentation of said distinguished region dependent on the detected position of said at least one finger.

5. A method as claimed in claim 1 comprising displaying said fusion image in said presentation area with at least one region at an edge of said presentation area, and detecting a beginning of a movement of said at least one finger on said region and altering presentation of said fusion image dependent on said movement at least in a portion of said fusion image associated with said region.

6. A method as claimed in claim 1 comprising detecting said movement of said at least one finger with an infrared sensor integrated in said presentation area.

7. A device for selectively presenting two different first and second images, respectively obtained from a first image data set and a second image data set that is different from said first image data set, either individually or combined as a fusion image, comprising:
  a computerized display device presentation area having a first side and a second side perpendicular to said first side;
  a detector at said presentation area that detects movement of at least one finger of a user over or in contact with a surface of said presentation area;
  a processor connected to said display device, said processor being configured, when one of said first or second images is currently displayed in said presentation area, as a currently-displayed image, and movement of said at least one finger in a direction parallel to said first side is detected, in response to no more than said movement of said at least one finger in said direction parallel to said first side of said presentation area, to automatically remove said currently displayed image from said presentation area and displaying only the other of said first and second images;
  said processor also being configured, when one of said first and second images is currently displayed in said presentation area as an initially displayed image, and movement of said at least one finger in a first direction parallel to said second side of said presentation area is detected, in response to no more than said movement of said at least one finger in said first direction parallel to said second side of said presentation area, automatically to add the other of said first and second images to said initially displayed image in said presentation area to form a fusion image of said first and second images in said presentation area; and
  said processor also being configured, when said fusion image is displayed in said presentation area, and movement of said at least one finger in a second direction, opposite to said first direction, parallel to said second side is detected, in response to no more than said movement of said at least one finger in said second directional parallel to said second side of said presentation area, to remove the other of said first and second images from said fusion image to leave only said initially displayed image in said presentation area.

8. A device as claimed in claim 7 wherein said processor is configured to automatically time an elapsed time after changing from said currently displayed image to display of said other of said first and second images in said presentation area, and to automatically revert to presentation of said currently displayed image after a predetermined elapsed time.

9. A device as claimed in claim 7 wherein said processor is configured to automatically time an elapsed time after removal of said other of said first and second images from said fusion image, and to automatically restore presentation of said fusion image to said presentation area after a predetermined elapsed time.

10. A device as claimed in claim 7 wherein said processor is configured to display said first image in said presentation area with a distinguished region that is selectable by detecting a position of said at least one finger relative to said surface of said presentation area, and to modify presentation of said distinguished region dependent on the detected position of said at least one finger.

11. A device as claimed in claim 7 wherein said processor is configured to display said fusion image in said presentation area with at least one region at an edge of said presentation area, and to detect a beginning of a movement of said at least one finger on said region and to alter presentation of said fusion image dependent on said movement at least in a portion of said fusion image associated with said region.

12. A device as claimed in claim 7 comprising an infrared sensor integrated in said presentation area that detects said movement of said at least one finger.

13. A method as claimed in claim 1 comprising automatically detecting, as said movement of said at least one finger in a direction parallel to said first side, a sliding movement of at least one finger in said direction parallel to said first side, and detecting, as said movement of said at least one finger in a first direction parallel to said second side of said presentation area, a sliding movement of at least one finger in said first direction parallel to said second side of said presentation area, and detecting, as said movement of said at least one finger in a second direction, opposite to said first direction, parallel to said second side of said presentation area, a sliding movement of at least one finger in said second direction, opposite to said first direction, parallel to said second side of said presentation area.

14. A method as claimed in claim 13 comprising responding, in said computerized display device, to a respective sliding movement of said at least one finger only when a magnitude of the respective sliding movement exceeds a predetermined magnitude threshold.

15. A device as claimed in claim 7 wherein said processor is configured to automatically detect, as said movement of said at least one finger in a direction parallel to said first side, a sliding movement of at least one finger in said direction parallel to said first side, and to detect, as said movement of said at least one finger in a first direction parallel to said second side of said presentation area, a sliding movement of at least one finger in said first direction parallel to said second side of said presentation area, and to detect, as said movement of said at least one finger in a second direction, opposite to said first direction, parallel to said second side of said presentation area, a sliding movement of at least one finger in said second direction, opposite to said first direction, parallel to said second side of said presentation area.

16. A device as claimed in claim 7 wherein said processor is configured to respond to a respective sliding movement of said at least one finger only when a magnitude of the respective sliding movement exceeds a predetermined magnitude threshold.

* * * * *